(12) United States Patent
Cummings

(10) Patent No.: US 12,697,013 B2
(45) Date of Patent: Aug. 4, 2026

(54) VALVE AND VALVE COMPONENTS FOR AN ENDOSCOPE

(71) Applicant: Boston Scientific Scimed, Inc., Maple Grove, MN (US)

(72) Inventor: Nathan Thomas Cummings, Worcester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 290 days.

(21) Appl. No.: 18/487,314

(22) Filed: Oct. 16, 2023

(65) Prior Publication Data

US 2024/0122450 A1     Apr. 18, 2024

Related U.S. Application Data

(60) Provisional application No. 63/416,708, filed on Oct. 17, 2022.

(51) Int. Cl.
A61B 1/00 (2006.01)
A61B 1/015 (2006.01)

(52) U.S. Cl.
CPC .......... A61B 1/00068 (2013.01); A61B 1/015 (2013.01)

(58) Field of Classification Search
CPC ............................ A61B 1/00068; A61B 1/015
See application file for complete search history.

(56) References Cited

U.S. PATENT DOCUMENTS

| | | | |
|---|---|---|---|
| 3,103,231 A | 9/1963 | Moen | |
| 4,562,830 A | 1/1986 | Yabe | |
| 5,257,773 A | 11/1993 | Yoshimoto et al. | |
| 6,123,094 A | 9/2000 | Breda | |
| 6,254,061 B1 * | 7/2001 | Levine ............... A61B 1/00135 | |
| | | | 251/324 |
| 6,286,179 B1 | 9/2001 | Byrne | |
| 6,887,193 B2 | 5/2005 | Bacher et al. | |
| 9,161,680 B2 | 10/2015 | Bellofatto et al. | |
| 9,307,890 B2 | 4/2016 | Ouchi | |
| 10,865,893 B2 * | 12/2020 | Marks ...................... F16K 3/26 | |
| 11,246,471 B2 | 2/2022 | Grudo et al. | |

(Continued)

FOREIGN PATENT DOCUMENTS

| | | | |
|---|---|---|---|
| AU | 2020311423 A1 | 11/2021 | |
| JP | 2021-523852 A | 9/2021 | |
| WO | 2019226094 A1 | 11/2019 | |

OTHER PUBLICATIONS

International Search Report and Written Opinion dated Jan. 23, 2024 for International Application No. PCT/US2023/076948.

*Primary Examiner* — Michael J Carey
*Assistant Examiner* — Megan Elizabeth Monahan
(74) *Attorney, Agent, or Firm* — Seager, Tufte & Wickhem, LLP

(57)     ABSTRACT

Devices, systems, and methods for a valve for a medical device. The valve may include a valve stem. An elongate body of the valve stem may include a first opening and a second opening fluidly coupled to one another via a lumen. The valve stem may include one or more seals extending circumferentially around the elongate body. The one or more seals may include sealing surfaces that may be non-perpendicular with a longitudinal axis of the elongate body to selectively fluidly isolate openings or other features of a valve well in which the valve stem is configured to translate.

19 Claims, 9 Drawing Sheets

(56)         References Cited

U.S. PATENT DOCUMENTS

2015/0011831 A1 *   1/2015  Ouchi ..................... A61B 1/05
                                                    600/159
2020/0016637 A1     1/2020  Still et al.
2020/0352415 A1    11/2020  Harris et al.
2020/0355281 A1 *  11/2020  Harris ............... A61B 1/00068
2022/0186846 A1     6/2022  Harris et al.

* cited by examiner

VALVE AND VALVE COMPONENTS FOR AN ENDOSCOPE

CROSS-REFERENCE TO RELATED APPLICATIONS

This application claims the benefit of U.S. Provisional Patent Application Ser. No. 63/416,708 filed on Oct. 17, 2022, the disclosure of which is incorporated herein by reference.

TECHNICAL FIELD

This disclosure relates generally to valve assemblies and methods, and particularly to valve stems, seals, and methods for an endoscope.

BACKGROUND

A wide variety of intracorporeal medical devices and systems have been developed for medical use, for example, for endoscopic procedures. Some of these devices and systems include guidewires, catheters, catheter systems, endoscopic instruments, and the like. These devices and systems are manufactured by any one of a variety of different manufacturing methods and may be used according to any one of a variety of methods. Of the known medical devices, systems, and methods, each has certain advantages and disadvantages. There is an ongoing need to provide alternative medical devices and systems as well as alternative methods for manufacturing and using medical devices and systems.

SUMMARY

This disclosure provides design, material, manufacturing method, and use alternatives for medical devices and medical systems. In a first example, a valve stem for a medical device may comprise an elongate body, a first opening in the elongate body, a second opening in the elongate body, a lumen extending from the first opening to the second opening, and a seal extending circumferentially around the elongate body and defining a sealing surface. In some cases, the sealing surface may be non-perpendicular with a longitudinal axis of the elongate body.

Alternatively or additionally to any of the examples above, the valve stem may further include a groove defining a surface of the elongate body and extending circumferentially around the elongate body, and the groove may be non-perpendicular with the longitudinal axis of the elongate body and the seal is within the groove.

Alternatively or additionally to any of the examples above, the sealing surface may be planar.

Alternatively or additionally to any of the examples above, the sealing surface may be non-planar.

Alternatively or additionally to any of the examples above, the sealing surface may be a wave having two peaks and two valleys.

Alternatively or additionally to any of the examples above, the seal may be a first seal and the sealing surface is a first sealing surface and the valve stem further comprises a second seal extending circumferentially around the elongate body and defining a second sealing surface, and the second sealing surface may be non-perpendicular with the longitudinal axis of the elongate body.

Alternatively or additionally to any of the examples above, the first sealing surface is parallel to the second sealing surface.

Alternatively or additionally to any of the examples above, the first sealing surface may be non-parallel to the second sealing surface.

Alternatively or additionally to any of the examples above, the valve stem may further include a third seal extending circumferentially around the elongate body and defining a third sealing surface, and wherein the third sealing surface is non-perpendicular with the longitudinal axis of the elongate body.

Alternatively or additionally to any of the examples above, the elongate body and the seal may be monolithic.

Alternatively or additionally to any of the examples above, the elongate body may be formed from a thermoplastic elastomer (TPE).

In another example, a valve stem for a medical device may be configured to translate within a valve well of the medical device and may comprise an elongate body, a first opening in the elongate body, a second opening in the elongate body, a lumen extending from the first opening to the second opening, a first seal extending circumferentially around the elongate body and defining a first sealing surface, the first seal is proximal of the first opening, and a second seal extending circumferentially around the elongate body and defining a second sealing surface, the first seal may be distal of the of the first opening, and the first sealing surface and the second sealing surface may be non-perpendicular with a longitudinal axis of the elongate body.

Alternatively or additionally to any of the examples above, one or both of the first sealing surface and the second sealing surface may be planar.

Alternatively or additionally to any of the examples above, one or both of the first sealing surface and the second sealing surface may be non-planar.

Alternatively or additionally to any of the examples above, the valve stem may further include a third seal extending circumferentially around the elongate body and defining a third sealing surface, and one or more of the first sealing surface, the second sealing surface, and the third sealing surface may be parallel to a least one other of the first sealing surface, the second sealing surface, and the third sealing surface.

In another example, a medical device may comprise a proximal handle, a distal tip unit adapted to be inserted into a body cavity of a patient, an elongate tube extending between the proximal handle and the distal tip unit, and a valve in communication with a lumen of the elongate tube to adjust a fluid flow to the distal tip unit via the lumen, the valve comprises a valve well having an interior wall, a first opening, and a second opening; and a valve stem configured to adjust within the valve well, the valve stem comprising an elongate body and a seal defining a sealing surface extending circumferentially around the elongate body, and the sealing surface may be configured to engage the interior wall at a first location proximal of the first opening and at a second location distal of the second opening, the second location is circumferentially spaced from the first location.

Alternatively or additionally to any of the examples above, the sealing surface may be planar.

Alternatively or additionally to any of the examples above, the sealing surface may be non-planar.

Alternatively or additionally to any of the examples above, the elongate body may include a groove defining an outer surface of the elongate body and extending circumferentially around the elongate body, and the seal may extend circumferentially around the elongate body within the groove.

Alternatively or additionally to any of the examples above, the seal may be a first seal and the sealing surface is a first sealing surface, the valve stem may further comprise a second seal extending circumferentially around the elongate body and defining a second sealing surface, and the second sealing surface may be configured to engage the interior wall at a location distal of the first opening and the second opening.

These and other features and advantages of the present disclosure will be readily apparent from the following detailed description, the scope of the claimed invention being set out in the appended claims.

BRIEF DESCRIPTION OF THE DRAWINGS

The accompanying drawings, which are incorporated in and constitute a part of this specification, illustrate various embodiments and together with the description serve to explain the principles of the present disclosure.

Figure 1:
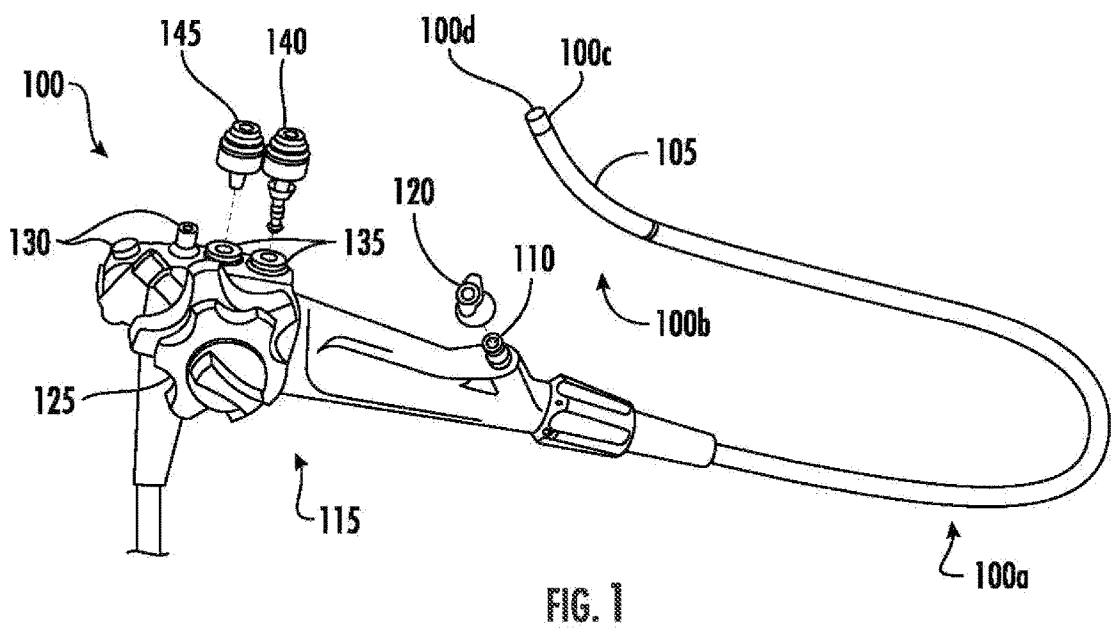
FIG. 1 depicts a schematic view of components of an illustrative endoscope.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

This disclosure is now described with reference to an illustrative medical system that may be used in endoscopic medical procedures. However, it should be noted that reference to this particular procedure is provided only for convenience and not intended to limit the disclosure. A person of ordinary skill in the art would recognize that the concepts underlying the disclosed devices and related methods of use may be utilized in any suitable procedure, medical or otherwise. This disclosure may be understood with reference to the following description and the appended drawings, wherein like elements are referred to with the same reference numerals.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about"

may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5). Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is illustrative only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The detailed description is intended to illustrate but not limit the disclosure. Those skilled in the art will recognize that the various elements described may be arranged in various combinations and configurations without departing from the scope of the disclosure. The detailed description illustrates example embodiments of the disclosure.

Figure 2:
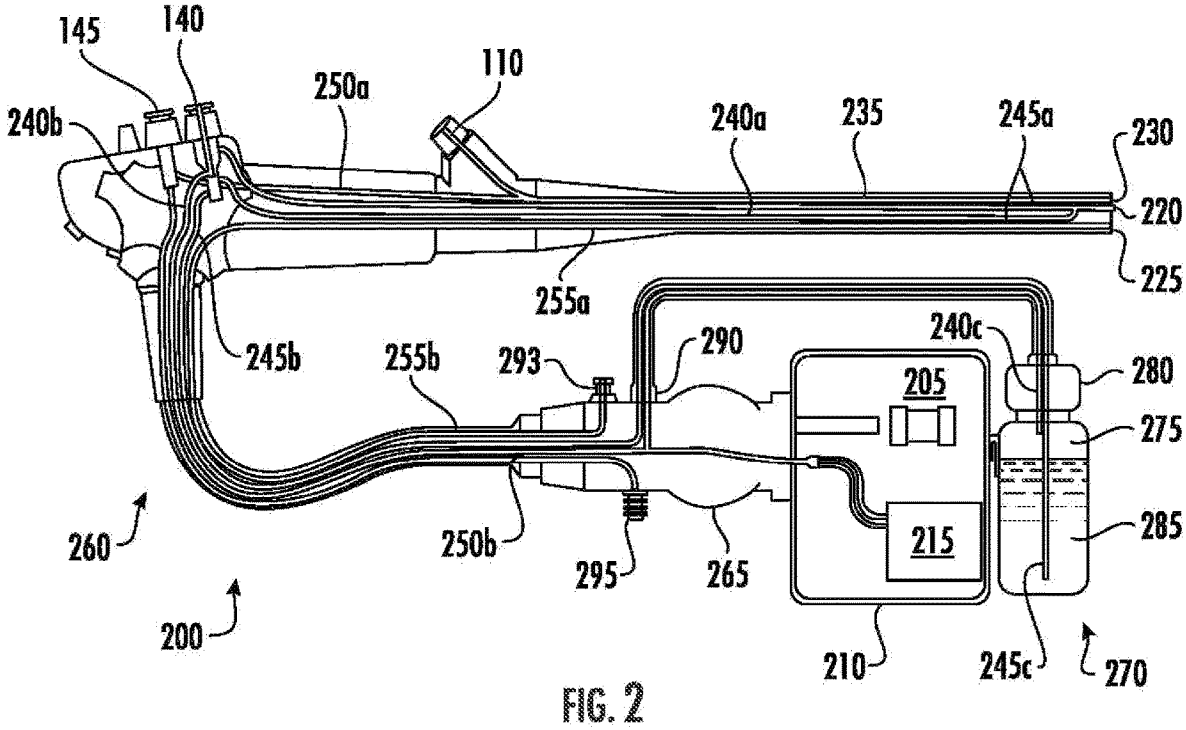
FIG. 2 depicts a schematic view of components of an illustrative endoscope system.

With reference to FIG. 1, an illustrative endoscope 100 is depicted and FIG. 2 depicts an illustrative endoscope system 200. The endoscope 100 may include an elongated tube or shaft 100a that is configured to be inserted into a subject (e.g., a patient).

A light source 205 of the endoscope system 200 may feed illumination light to a distal portion 100b of the endoscope 100. The distal portion 100b of the endoscope 100 may house an imager (e.g., CCD or CMOS imager) (not shown). The light source 205 (e.g., lamp) may be located in a video processing unit 210 that processes signals input from the imager and outputs processed video signals to a video monitor (not shown) for viewing. The video processing unit 210 may also serve as a component of an air/water feed circuit by housing a pressurizing pump 215, such as an air feed pump, in the unit 210.

The endoscope shaft 100a may include a distal tip 100c (e.g., a distal tip unit adapted to be inserted into a body cavity of a patient) provided at the distal portion 100b of the shaft 100a and a flexible bending portion 105 proximal to the distal tip 100c. The flexible bending portion 105 may include an articulation joint (not shown) to assist with steering the distal tip 100c. On an end face 100d of the distal tip 100c of the endoscope 100 is a gas/lens wash nozzle 220 for supplying gas to insufflate the interior of the patient at the treatment area and for supplying water to wash a lens covering the imager. An irrigation opening 225 in the end face 100d supplies irrigation fluid to the treatment area of the patient. Illumination windows (not shown) that convey illumination light to the treatment area, and an opening 230 to a working channel 235 extending along the shaft 100a for passing tools to the treatment area, may also be included on the face 100d of the distal tip 100c. The working channel 235 may extend along the shaft 100a to a proximal channel opening 110 positioned distal to an operating handle 115 (e.g., a proximal handle) of the endoscope 100. A biopsy valve 120 may be utilized to seal the channel opening 110 against unwanted fluid egress.

The operating handle 115 may be provided with knobs 125 for providing remote 4-way steering of the distal tip via wires connected to the articulation joint in the bendable flexible portion 105 (e.g., one knob controls up-down steering and another knob control for left-right steering). A plurality of video switches 130 for remotely operating the video processing unit 210 may be arranged on a proximal end side of the handle 115.

The handle 115 may be provided with dual valve locations 135. One of the valve locations 135 may have or receive a gas/water valve 140 for operating an insufflating gas and lens water feed operation. A gas supply line 240a and a lens wash supply line 245a run distally from the gas/water valve 140 along the shaft 100a and converge at the distal tip 100c proximal to the gas/wash nozzle 220, as depicted in FIG. 2.

The other valve location 135 may have or receive a suction valve 145 for operating a suction operation. A suction supply line 250a may run distally from the suction valve 145 along the shaft 100a to a junction point in fluid communication with the working channel 235 of the endoscope 100.

The operating handle 115 may be electrically and fluidly connected to the video processing unit 210, via a flexible umbilical 260 and connector portion 265 extending therebetween. The flexible umbilical 260 has a gas (e.g., air or $CO_2$) feed line 240b, a lens wash feed line 245b, a suction feed line 250b, an irrigation feed line 255b, a light guide (not shown), and an electrical signal cable (not shown). The connector portion 265 when plugged into the video processing unit 210 connects the light source 205 in the video processing unit with the light guide. The light guide runs along the umbilical 260 and the length of the endoscope shaft 100a to transmit light to the distal tip 100c of the endoscope 100. The connector portion 265 when plugged into the video processing unit 210 also connects the air pump 215 to the gas feed line 240b in the umbilical 260.

A water reservoir or container 270 (e.g., water bottle and/or other suitable reservoir or container) may be fluidly connected to the endoscope 100 through the connector portion 265 and the umbilical 260. A length of gas supply tubing 240c passes from one end positioned in an air gap 275 between the top 280 (e.g., bottle cap) of the reservoir 270 and the remaining water 285 in the reservoir to a detachable gas/lens wash connection 290 on the outside of the connector portion 265. The gas feed line 240b from the umbilical 260 branches in the connector portion 265 to fluidly communicate with the gas supply tubing 240c at the detachable gas/lens wash connection 290, as well as the air pump 215. A length of lens wash tubing 245c, with one end positioned at the bottom of the reservoir 270, may pass through the top 280 of the reservoir 270 to the same detachable connection 290 as the gas supply tubing 240c on the connector portion 265. In other embodiments, the connections may be separate and/or separated from each other. The connector portion 265 may also have a detachable irrigation connection 293 for irrigation supply tubing (not shown) running from a source of irrigation water (not shown) to the irrigation feed line 255b in the umbilical 260. In some embodiments, irrigation water is supplied via a pump (e.g., peristaltic pump) from a water source independent (not shown) from the water reservoir 270. In other embodiments, the irrigation supply tubing and lens wash tubing 245c may source water from the same reservoir. The connector portion 265 may also include a detachable suction connection 295 for suction feed line 250b and suction supply line 250a fluidly connecting a vacuum source (e.g., hospital house suction) (not shown) to the umbilical 260 and endoscope 100.

The gas feed line 240b and lens wash feed line 245b may be fluidly connected to the valve location 135 for the gas/water valve 140 and configured such that operation of the gas/water valve 140 in the well controls supply of gas or lens wash to the distal tip 100c of the endoscope 100. The suction feed line 250b is fluidly connected to the valve location 135 for the suction valve 145 and configured such that operation of the suction valve 145 in the well controls suction applied to the working channel 235 of the endoscope 100.

Referring to FIG. 2, an illustrative operation of an endoscope system 200, including an endoscope such as endoscope 100 above, is explained. Air from the air pump 215 in the video processing unit 210 may flow through the connector portion 265 and branch to the gas/water valve 140 on the operating handle 115 through the gas feed line 240b in the umbilical 260, as well as through the gas supply tubing 240c to the water reservoir 270 via the connection 290 on the connector portion 265. When the gas/water valve 140 is in a neutral position, without the user's finger on the valve, air is allowed to flow out of the valve 140 to atmosphere. In a first position, the user's finger is used to block the vent to atmosphere. Gas is allowed to flow from the valve 140 down the gas supply line 240a and out the distal tip 100c of the endoscope 100 in order to, for example, insufflate the treatment area of the patient. When the gas/water valve 140 is pressed downward to a second position, gas is blocked from exiting the valve 140, allowing pressure of the air passing from the air pump 215 to rise in the water reservoir 270. Pressurizing the water source forces water out of the lens wash tubing 245c, through the connector portion 265, umbilical 260, through the gas/water valve 140 and down the lens wash supply line 245a, converging with the gas supply line 240a prior to exiting the distal tip 100c of the endoscope 100 via the gas/lens wash nozzle 220. Air pump pressure may be calibrated to provide lens wash water at a relatively low flow rate compared to the supply of irrigation water.

The volume of the flow rate of the lens wash is governed by gas pressure in the water reservoir 270. When gas pressure begins to drop in the water reservoir 270, as water is pushed out of the reservoir 270 through the lens wash tubing 245c, the air pump 215 replaces lost air supply in the reservoir 270 to maintain a substantially constant pressure, which in turn provides for a substantially constant lens wash flow rate. In some embodiments, a filter (not shown) may be placed in the path of the gas supply tubing 240c to filter-out undesired contaminants or particulates from passing into the water reservoir 270. In some embodiments, outflow check valves or other one-way valve configurations (not shown) may be placed in the path of the lens wash supply tubing to help prevent water from back-flowing into the reservoir 270 after the water has passed the valve.

A relatively higher flow rate compared to lens wash is typically required for irrigation water, since a primary use is to clear the treatment area in the patient of debris that obstructs the user's field of view. Irrigation is typically achieved with the use of a pump (e.g., peristaltic pump), as described. In configurations with an independent water source for irrigation, tubing placed in the bottom of a water source may be passed through the top of the water source and threaded through the head on the upstream side of the pump. Tubing on the downstream side of the pump 255c is connected to the irrigation feed line 255b in the umbilical 260 and the irrigation supply line 255a of endoscope 100 via the irrigation connection 293 on the connector portion 265. When irrigation water is required, fluid is pumped from the water source by operating the irrigation pump, such as by depressing a footswitch (not shown), and flows through the irrigation connection 293, through the irrigation feed line 255b in the umbilical 260, and down the irrigation supply line in the shaft 100a of the endoscope 100 to the distal tip 100c. In order to equalize the pressure in the water source as water is pumped out of the irrigation supply tubing, an air vent (not shown) may be included in the top 280 of the water reservoir 270. The vent allows atmospheric air into the water source preventing negative pressure build-up in the water source, which could create a vacuum that suctions undesired matter from the patient back through the endoscope toward the water source. In some configurations, outflow check valves or other one-way valve configurations (not shown), similar to the lens wash tubing 245c, may be placed in the path of the irrigation supply tubing to help prevent back-flow into the reservoir after water has passed the valve.

The suction valve 145 may be configured to allow or prevent suction and/or a suction effect in the working channel 235. When the suction valve 145 is in a valve closed position (e.g., a first configuration), a suction fluid flow through the working channel 235 may be blocked by the suction valve 145. When suction is desired in the working channel 235, an operator or user may actuate the suction valve 145 (e.g., by depressing a button on the valve and/or actuating the suction valve 145 in one or more other suitable manners) in order to bring the suction valve 145 to a valve open position (e.g., a second configuration). When the suction valve 145 is in the valve opened position, a flow channel inside the suction valve may connect the working channel 235 to the suction device coupled to suction connection 295 and the suction device may create a negative pressure that draws fluid into and out of the working channel 235 through an outlet provided in the suction valve. When the operator or user releases the suction valve 145, the valve 145 may return to its valve closed position and reduce or block a suction fluid flow from the working channel 235.

In some cases, suction valves 145 may rely on a path of least resistance to direct a suction fluid flow through the endoscope system 200. In some cases, when a suction pump is turned on for a procedure, the pump remains on for an entirety of the procedure and continually pulls air from the flexible umbilical 260, which in turn draws fluid from the line side of the endoscope 100 that runs up the umbilical 260 and connects to a port at the suction valve 145. When the suction valve 145 is in a first position and/or configuration (e.g., a closed position) the suction force or negative pressure from the suction pump is blocked from the working channel 235 and may pull fluid from atmosphere through the suction valve 145. When the suction valve 145 is actuated to a second position and/or configuration (e.g., an opened position) (e.g., when the button or cap associated with the suction valve 145 is depressed and/or actuated in one or more other suitable manners), the opening from atmosphere through the suction valve 145 to the suction pump may be effectively closed or blocked by the suction valve 145 and a fluid path between working channel 235 and the suction pump through the suction valve 145 may be opened. Thus, fluid moving to the suction pump may follow a path of least resistance, where the path may change depending on whether the suction valve 145 is in a first position (e.g., a closed position) or a second position (e.g., an opened position)

In some cases, valve stems of the gas/water valve 140 and/or the suction valve 145 may be configured to have a close fit with a valve well configured to receive the valve stem in the endoscope 100. In such gas/water valves 140 and suction valves 145, when the valve stem is in a first position (e.g., a closed position) the close fit blocks a flow path or increases a resistance to flow between the working channel 235 and a fluid line (e.g., the gas feed line 240b, lens wash feed line 245b, suction feed line 250b) of the endoscope system 200. Similarly, when the valve stem is in a second position, the close fit opens a flow path and reduces a resistance to flow between the working channel 235 and the fluid lines.

The gas/water valve 140 and/or the suction valve 145 configured to block flow using close fits between the valve stem and valve well require valves stems that are precisely manufactured. The precision required to produce suction valves with close fits has required expensive materials (e.g., metals, etc.), highly precise machinery, is time consuming to achieve, and suffers from inconsistent manufacturing tolerances.

Additionally, valves with close fit valve stems and valve wells are manufactured to have at least some clearance to allow the valve stem to adjust positions within the valve well, which may lead to leakage. The leakage due to clearance between valve stems and valve wells may be exacerbated by openings in the valve well being closely positioned to one another. This clearance, which may result in leakage during use, may lead to at least two issues noticeable by a physician.

The first issue is when the valve is in a position intended to block flow from the working channel 235, there is still some flow passing through the working channel 235. The smaller the clearance between the valve stem and the valve well, the less unwanted flow through the working channel 235 that occurs and the larger the clearance, the more unwanted flow through the working channel 235, however, clearance is needed to facilitate movement of the valve stem within the valve well. When flow is actively moving through the working channel 235 in such configurations of the valve, users may perceive the suction as "poor insufflation" and/or experience leakage at the distal end of the endoscope shaft 100a, even when the valve is in a position intended to block a flow from the working channel 235.

The second issue is when a valve stem of the valve is in a position within a valve well to facilitate a flow between the working channel 235 and fluid lines, the desired flow may be insufficient or weaker than desired or anticipated due to fluid escaping through the clearances from its intended path. In one example, when a valve stem of the suction valve 145 is configured to have a close-fit with a valve well and is in a position within the valve well to facilitate a suction flow between the working channel 235 and the suction pump through the suction valve 145, the flow from atmosphere to the suction pump may not be completely blocked. Any such leaking from atmosphere may reduce a pressure differential between the suction valve 145 and the distal end of the working channel 235, which may lead to a reduced suction force or negative pressure, reduced flow rates, and aerated flow through the fluid path to the suction pump.

Valves configured to operate with close-fit valve stems and valve wells may work well enough when intended for re-use in multiple procedures, as a price point for such valves can be high enough to justify manufacturing the valves from materials and with the necessary precision that can achieve and maintain desired tolerances over the life of the reusable valves. However, a price point of a single use valve may not allow for use of the necessary materials, tools, and/or the precise manufacturing required to achieve and/or maintain tolerances over the life of single-use suction valves.

In some cases, compliant seals may be applied to a central shaft to form a valve stem that is configured to fully seal off flow paths through a valve in an endoscope, while reducing costs and not requiring as much manufacturing precision relative to valve stems configured to seal flow paths using a close-fit configuration with valve wells. When using compliant seals, the seals may be applied to the central shaft as discrete components and/or may be applied to the central shaft (e.g., a valve shaft or elongate body of a valve shaft) through insert-molding, over-molding, and/or other suitable application technique. However, such seals are applied in a plane perpendicular to a longitudinal axis of the central shaft and may not be usable in all situations. For example, due to openings of a valve well in which the valve stem is or is to be positioned being circumferentially spaced and axially overlapping or having edges proximate to the plane perpendicular to longitudinal axis of the central shaft, the seals that extend in a plane perpendicular to the longitudinal axis and over one or more of the openings may not fully seal-off such openings.

The valve configurations for endoscopes 100 and/or other suitable scopes discussed herein address the above-noted concerns with existing valves and are configured to mitigate and/or eliminate leakage across the valves. The valve configurations discussed with respect to FIGS. 3-12 may include valve stems that have one or more seals forming a sealing surface extending circumferentially around a central shaft or elongate body and non-perpendicular with a longitudinal axis of the elongate body.

Figure 3:
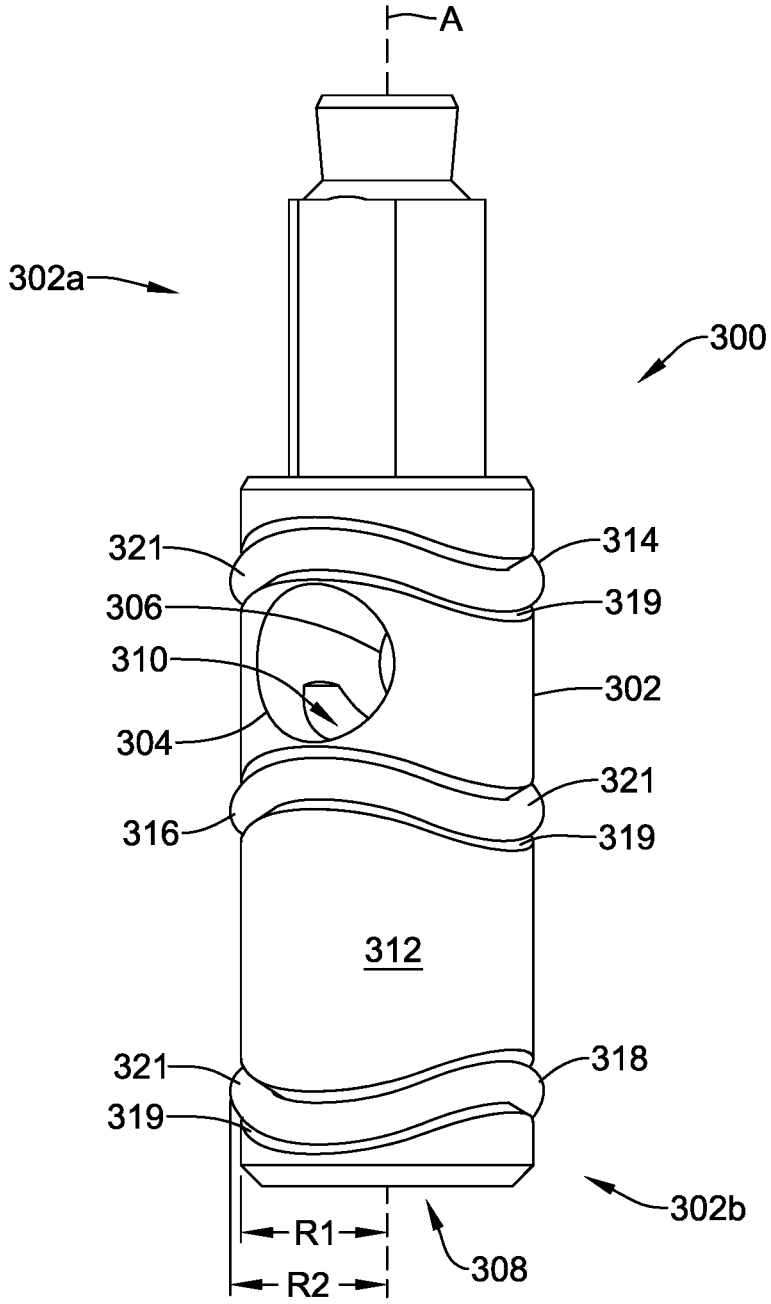
FIG. 3 depicts a schematic perspective view of an illustrative valve stem.

FIG. 3 depicts a perspective view of an illustrative valve stem 300 for use in an endoscope 100 (e.g., a medical device assembly). Although the valve stem 300 depicted in FIG. 3 may be configured for use in a suction valve 145, the valve stem 300 may be additionally or alternatively configured for use in a gas/water valve 140 and/or other suitable valves including features and/or properties to those of suction valves 145 and/or gas/water valves 140, but with seals and/or openings at different locations and configured for a particular purpose (e.g., where the seals and/or openings may be configured and/or positioned to adjustably align with openings of a valve well).

The valve stem 300 may have any suitable configuration configured to adjust positions within a valve well and/or adjustably fluidly couple the working channel 235 with fluid lines of the endoscope system 200. In one example, the valve stem 300 may be elongated and may include one or more openings and one or more lumens extending between the one or more openings.

The valve stem 300 depicted in FIG. 3 may include an elongate body 302. The elongate body 302 may include a first portion 302a and a second portion 302b. The first portion 302a of the elongate body 302 may be an engagement portion configured to be actuated to adjust a position of the valve stem 300 within a valve well.

In some cases, the first portion 302a may be configured to couple with a button or cap for the valve that a user may interact with to adjust a position of the valve stem 300 within the valve well, but this is not required. Example suitable coupling mechanisms for connecting the first portion 302a with a button or cap may include, but are not limited to, adhesives, a threaded connection, a luer lock connection, a snap connection, a ball-detent connector, a friction fit, and/or additional or alternative coupling mechanisms. The first portion 302a of the elongate body 302 may also include one or more "keying" features that are configured to engage keying features of a valve well to enable a desired orientation of the valve stem 300 within the valve well. The second portion 302b of the elongate body 302 may be configured to be positioned within the valve well and may include features for facilitating fluid flow between the working channel 235 and fluid lines of the endoscope system 200 and/or blocking fluid flow between the working channel 235 and the fluid lines.

The valve stem 300 may include one or more openings in the elongate body 302. In one example, as depicted in FIG. 3, the valve stem 300 may include a first opening 304 in the elongate body 302, a second opening 306 in the elongate body 302, and a third opening 308 in the elongate body 302, but other suitable configurations are contemplated. In some cases, one or more of the openings in the valve stem 300 may be radial or side openings and one or more openings may be axial or end openings. In the example depicted in FIG. 3, the first opening 304 and the second opening 306 may be radial openings located at a same, first axial location along a longitudinal axis A of the elongate body 302 and the third opening 308 may be an axial opening located at a second axial location along the longitudinal axis of the elongate body 302 that is distal of the first axial location. In some cases, an axial location of an opening may be based on or determined from a center of the opening.

The valve stem 300 may include one or more lumens extending between the one or more openings of the valve stem 300. As depicted in FIG. 3, a lumen 310 may extend between the third opening 308 and the first opening 304 and the second opening 306. Other suitable configurations of the lumen 310 and/or openings 304, 306, 308 that facilitate adjusting flow paths across a valve based on a position of the valve stem 300 relative to a valve well are contemplated.

The valve stem 300 may include one or more seals that are configured to translate with the valve stem 300 within a valve well. In one example, as depicted in FIG. 3, the valve stem 300 may include a first seal 314, a second seal 316, and a third seal 318 extending radially outward from the outer surface 312 of the elongate body 302, where the first seal 314 may be located proximal of the first opening 304 and the second opening 306, the second seal 316 may be located distal of the first opening 304 and the second opening 306, and the third seal 318 may be located distal of the second seal. Other suitable configurations of the seals of the valve stem 300 are contemplated.

Each of the seals 314, 316, 318 may include a sealing surface 321, where the sealing surface 321 is the portion of the seals 314, 316, 318 configured to engage the inner wall surface of the valve well. Although not required, the sealing surface 321 may be or may include the outer most portion of the seal 314, 316, 318. In some cases, the seals 314, 316, 318 and/or the sealing surfaces 321 thereof may be circumferentially symmetrical about one or more planes extending through the elongate body 302, but this is not required and the seals 314, 316, 318 and/or the sealing surface 321 may be circumferentially asymmetric.

In some cases, two or more of the seals 314, 316, 318 may be parallel to one another (e.g., have an equal distance between two or more of seals 314, 316, 318 along an entire perimeter of the seals 314, 316, 318). Alternatively or additionally, one or more of the seals 314, 316, 318 may be non-parallel to at least one other of the seals 314, 316, 318 (e.g., the one or more of the seals 314, 316, 318 may have a varying distance between them around the circumference of the seals 314, 316, 318). In one example, when the valve stem 300 includes the first seal 314, the second seal 316, and the third seal 314, the sealing surface 321 of the first seal 314 and the sealing surface 321 of the second sealing 316 may be parallel and non-planar and the sealing surface 321 of the third seal 318 may be planar and non-parallel with the sealing surface 321 of the first seal 314 and the second sealing 316.

The elongate body 302 and the seals 314, 316, 318 may be formed from any suitable materials. In one example, the elongate body 302 may be formed from one or more of metals, polymer, acrylonitrile butadiene styrene (ABS), polycarbonate, thermoplastic elastomers (TPE), thermoplastic polyurethane (TPU), liquid silicone rubber (LSR), and/or other suitable materials. In another example, the seals 314, 316, 318 may be formed from one or more of a resilient material, a polymer, thermoplastic elastomers (TPE), thermoplastic polyurethane (TPU), liquid silicone rubber (LSR), and/or other suitable materials.

In some cases, the elongate body 302 may be formed from a first material and the seals 314, 316, 318 may be formed from a second material, where the second material may be the same as or different than the first material. In one example, the elongate body 302 and the seals 314, 316, 318 may be monolithic or otherwise monolithically formed from a single material. In another example, the elongate body 302 may be formed from a hard or rigid polymer and the seals

314, 316, 318 may be formed from a flexible and/or resilient polymer, but this is not required.

The material of the seals 314, 316, 318 may be resilient and may have any suitable durometer. In one example, the material of the seals 179 when formed on or part of the elongate body 302 may have a durometer in a range of about 20-80 shore A, about 30-60 shore A, about 50-75 shore A, and/or other suitable values within one or more other suitable ranges of durometer, but could be softer or firmer depending on the geometry used for the seals and the amount of interference desired between the seals 314, 316, 318 and an inner surface of a valve well. In one example, the seals 314, 316, 318 may be formed from silicone with a durometer in a range of 50-75 shore A, but this is not required.

The seals 314, 316, 318 may have any suitable shape configured to form a barrier to fluid along a space between the elongate body 302 and an inner wall of a valve well. For example, suitable shapes and/or configurations of the seals 314, 316, 318 may include, but are not limited to, o-rings (e.g., circular cross-sections), flat o-rings, X-shaped cross-sectional o-rings, wiper seal rings, disc shaped rings, pre-configured seals applied to the circumferentially extended recesses, and/or other suitable shapes and/or configurations of the seals 314, 316, 318.

The seals 314, 316, 318 of the valve stem 300 may be configured about the elongate body 302 in any suitable manner for interacting with (e.g., contacting) and/or maintaining contact with an inner wall or walls of a valve well in which the valve stem 300 is configured to adjust positions to create a barrier to fluid flow. Illustratively, the seals 314, 316, 318 may extend entirely or at least partially circumferentially around the elongate body 302 of the valve stem 300 and may extend radially outward from an outer surface 312 of the elongate body 302. For example, the seals 314, 316, 318 may have a radius R2 between a central longitudinal axis A of the elongate body 302 and an outer most portion of the seal 314, 316, 318 that may be greater than a radius R1 between the central longitudinal axis A and the outer surface 312 of the elongate body 302.

The sealing surface 321 and/or the seals 314, 316, 318 may be or may be configured to be non-perpendicular with the central longitudinal axis A of the elongate body 302. The sealing surface 321 and/or the seals 314, 316, 318 may be non-perpendicular (e.g., may be circumferentially non-perpendicular) to the central longitudinal axis A when portions of (e.g., points on) an outer-most circumference of the sealing surface 321 (e.g., an outer-most circumferential line around a seal 314, 316, 318 when the seal has a rounded or circular cross-section) and/or other circumferential portions of the seals 314, 316, 318 configured to engage the inner wall surface of the valve are located at different axial positions along the central longitudinal axis A from one another. The non-perpendicular sealing surface and/or seals 31, 316, 318 are described below in greater detail with respect to FIGS. 8-12.

The sealing surfaces 321 and/or the seals 314, 316, 318 that are circumferentially non-perpendicular with the central longitudinal axis A may be planar or non-planar. In one example, a planar sealing surface 321 and/or seals 314, 316, 318 being circumferentially non-perpendicular with the central longitudinal axis A may have all points on an outer-most circumference thereof (e.g., an outer-most circumferential line around a seal 314, 316, 318 when the seal has a rounded or circular cross-section) be in a single plane. In another example, a non-planar sealing surface 321 and/or seals 314, 316, 318 being circumferentially non-perpendicular with the central longitudinal axis A may have points on an outer-most circumference thereof in two or more planes, where at least one of the planes is non-perpendicular with the longitudinal axis A. In one example, when the non-planar sealing surface 321 is in a wave configuration, the sealing surface 321 may have two peaks and two valleys with outer-most circumferential points of the sealing surface 321 being in two or more different planes, but this is not required. Further, although not required, the sealing surfaces 321 may be symmetrical about at least one plane dividing the elongate body 302 in half. The planar and non-planar sealing surface and/or seals 31, 316, 318 are described below in greater detail with respect to FIGS. 8-12.

In some cases, the seals 314, 316, 318 may be positioned in recessed portions 319 and/or may include recessed portions 319 (e.g., grooves defining a surface of the elongate body 302 and/or other suitable recessed portions) proximate the seals 314, 316, 318. The recessed portions 319 (e.g., grooves) depicted in FIG. 3 may extend circumferentially around the elongate body 302 and may define a path configured to receive a seal 314, 316, 318, while providing space for seals 314, 316, 318 to flex in response to a sealing surface 321 of the seal 314, 316, 318 engaging an inner wall surface of a valve well. Alternatively or additionally, the recessed portions 319 may be configured to be proximate one or more of the seals 314, 316, 318 to provide space for seals 314, 316, 318 to flex in response to a sealing surface 321 of the seal 314, 316, 318 engaging an inner wall surface of a valve well. For example, when the seals 314, 316, 318 are formed monolithically with the elongate body 302, the recessed portions 319 may extend along each seal at one or both of the proximal and distal sides of the seals 314, 316, 318 to provide space for the seals 314, 316, 318 to flex in response to a sealing surface 321 of the seals 314, 316, 318 engaging an inner wall surface of a valve well.

The recessed portions 319 may have any suitable configuration. In some cases, one or more recessed portions 319 may have a cross-section that is entirely perpendicular with the central longitudinal axis A of the elongate body 302 and may be sized (e.g., may have a width between proximal and distal edges thereof at the outer surface 312 of the elongate body 302) to accommodate a seal that extends circumferentially around the elongate body 302 and has a sealing surface that is preformed to be non-perpendicular with the longitudinal axis A of the elongate body 302 when the seal is applied to the elongate body 302. Alternatively or additionally, the one or more recessed portions 319 may have a seal receiving surface that is non-perpendicular with the longitudinal axis A of the elongate body 302.

When a recessed portion 319 having a seal receiving surface (e.g., a surface of the elongate body 302 in the recessed portion 319 that is configured to receive a seal) that is non-perpendicular with the longitudinal axis A, the seal 314, 316, 318 received in the recessed portion 319 may have any annular shape and be resilient such that the it takes on the shape of the recessed portion 319 when it is applied to the elongate body 302 so as to create a sealing surface 321 that is non-perpendicular with the longitudinal axis A. Alternatively, the seal 314, 316, 318 may be pre-formed to have a sealing surface 321 that is non-perpendicular to the longitudinal axis A that matches a shape of the seal receiving surface of the recessed portion 319 that is non-perpendicular to the longitudinal axis A.

The recessed portions 319 may have any suitable cross-sectional shape. In some cases, the recessed portions 319 may have a v-shaped cross-section, a u-shaped cross section, a rounded cross-section, and/or other suitable cross-sectional shapes. In one example, the recessed portions 319 may have axially inward tapering proximal and distal sidewalls that have an axially inward end that terminates at a vertical bottom surface of the recessed portions 319 (e.g., as depicted in FIG. 4), but other suitable configurations are contemplated.

As discussed in greater detail below, the elongate body 302 and the seals 314, 316, 318 may be monolithic. When the valve stem 300 is monolithically configured, the recesses 319 may extend circumferentially around the elongate body 302 at locations proximate the seals 314, 316, 318 (e.g., at locations proximate to and proximal and/or distal of the seals 314, 316, 318) to provide space for the seals 314, 316, 318 to flex or bend when engaging the inner wall of the valve well.

Figure 4:
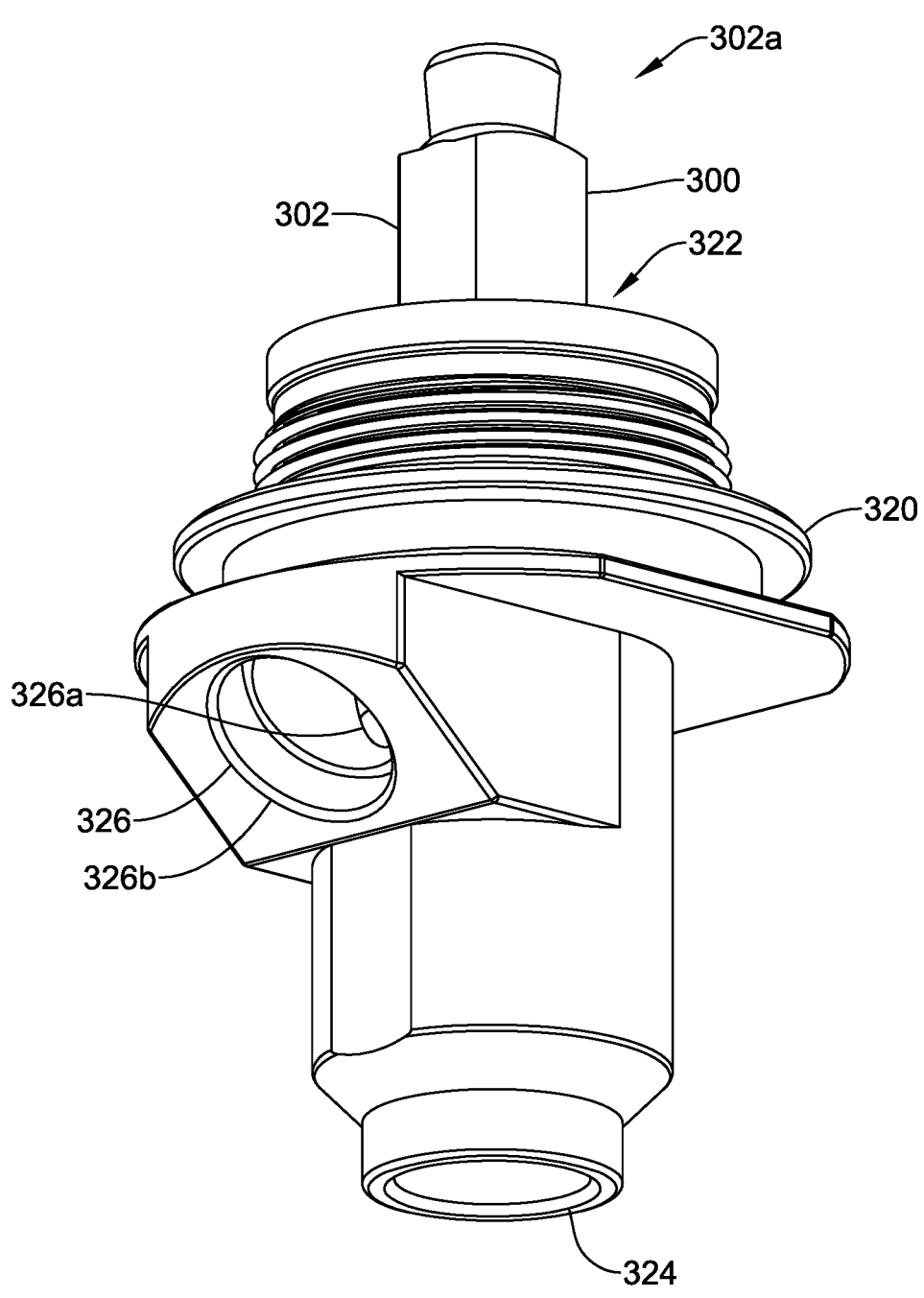
FIG. 4 depicts a schematic perspective view of an illustrative valve assembly.

FIG. 4 depicts a schematic perspective the illustrative valve stem 300 depicted in FIG. 3 within a valve well 320. The valve well 320 may have one or more openings including, for example, a proximal opening 322 (e.g., a first opening) configured to receive the valve stem 300, a distal opening 324 (e.g., a second opening), and an intermediate opening 326 (e.g., a third opening), where the intermediate opening 326 may extend from a proximal location 326a to a distal location 326b. Alternatively or additionally, the valve well 320 may take on one or more other suitable configurations.

Figure 5:
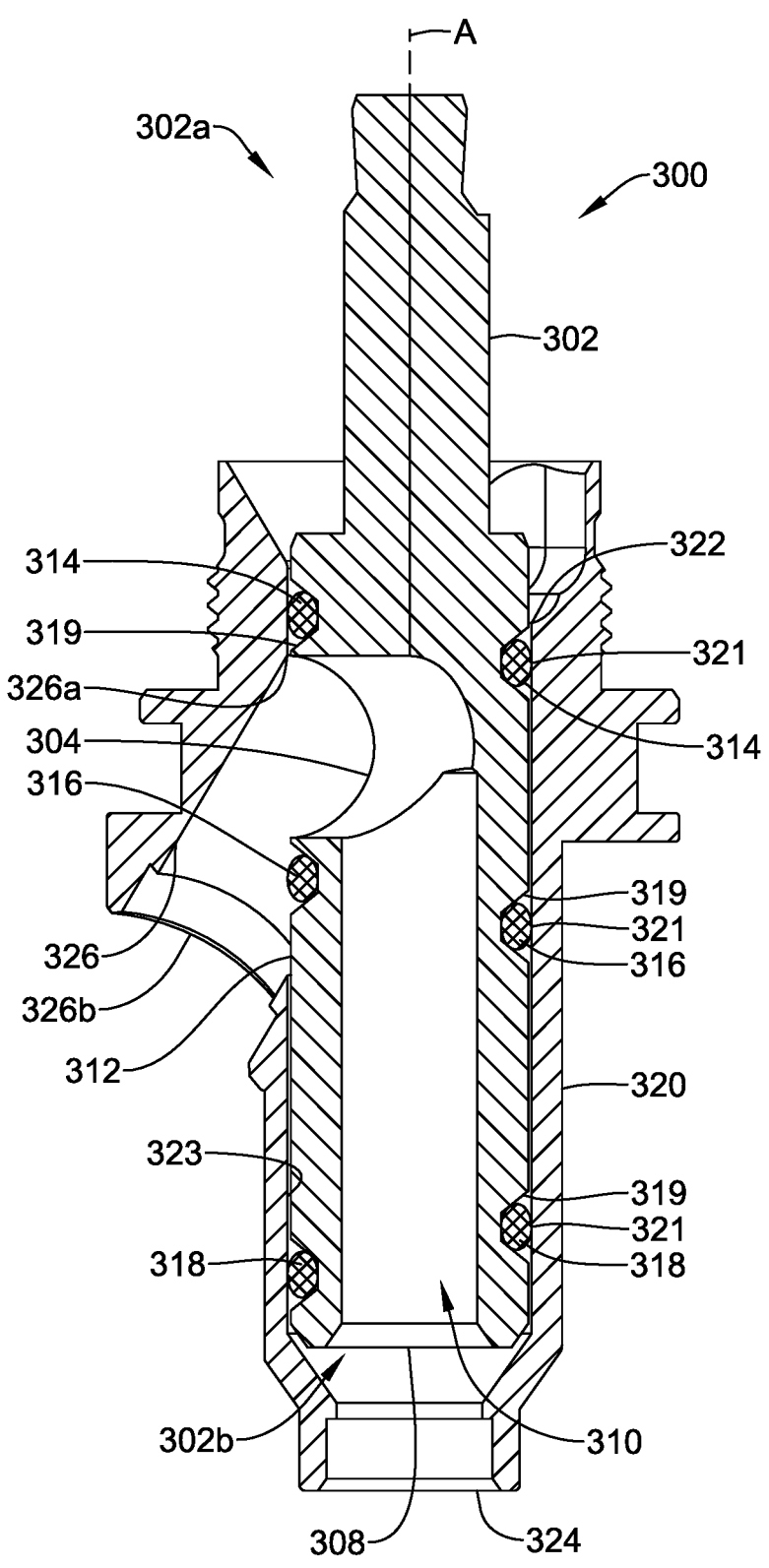
FIG. 5 depicts a schematic cross-section, quarter view of the illustrative valve assembly depicted in FIG. 4.

FIG. 5 depicts a schematic cross-sectional quarter (e.g., a ninety-degree) view of the illustrative valve stem 300 in the valve well 320 depicted in FIG. 4. The valve well 320 may have an inner wall 323 extending between the one or more openings of the valve well 320. For example, as discussed above, the inner wall 323 of the valve well 320 may extend between (e.g., be in fluid communication with) the proximal opening 322 configured to allow for translation of the valve stem 300 within the valve well 320, the distal opening 324 configured to couple with a first tubing of the endoscope system 200, and the intermediate opening 326 configured to couple with a second tubing of the endoscope system 200. The intermediate 326 opening may extend from the proximal location 326a at a lumen of the valve well 320 to the distal location 326b configured to couple with the second tubing of the endoscope system 200. The lumen of the valve well 320 may be at least partially defined by the inner wall 323 configured to receive the valve stem 300 for translation therein.

In some cases, one or more of the seals 314, 316, 318 may have sealing surfaces 321 configured to be non-perpendicular with the longitudinal axis A of the elongate body 302 based on locations of one or more openings in the valve well 320. For example, as depicted in FIG. 5, the sealing surface 321 of the seals 314, 316, 318 may be non-perpendicular with the longitudinal axis A because of limited axial spacing, if any, between the circumferentially-spaced proximal opening 322 and intermediate opening 326 (and/or between other suitable openings or features) of the valve well 320. In one example, axial spacing between a distal end of the proximal opening 322 of the valve well 320 and a proximal end of the intermediate opening 326 may be about 0.020 inches and the first seal 314 may be configured to have a portion of the sealing surface 321 that is non-perpendicular to the longitudinal axis A engage a surface of the inner wall 323 of the valve well 320 proximal of the proximal location 326a of the intermediate opening 326 and a portion of the sealing surface 321 engage the surface of the inner wall 323 distal of the proximal opening 322 of the valve well 320 to prevent fluid from passing between atmosphere and the distal opening 324 and/or the intermediate opening 326. In some cases, the keying features of the first portion 302a of the elongate body 302 may facilitate aligning a specified portion of the sealing surface 321 with an associated opening of the valve well 320, but this is not required.

Figure 6:
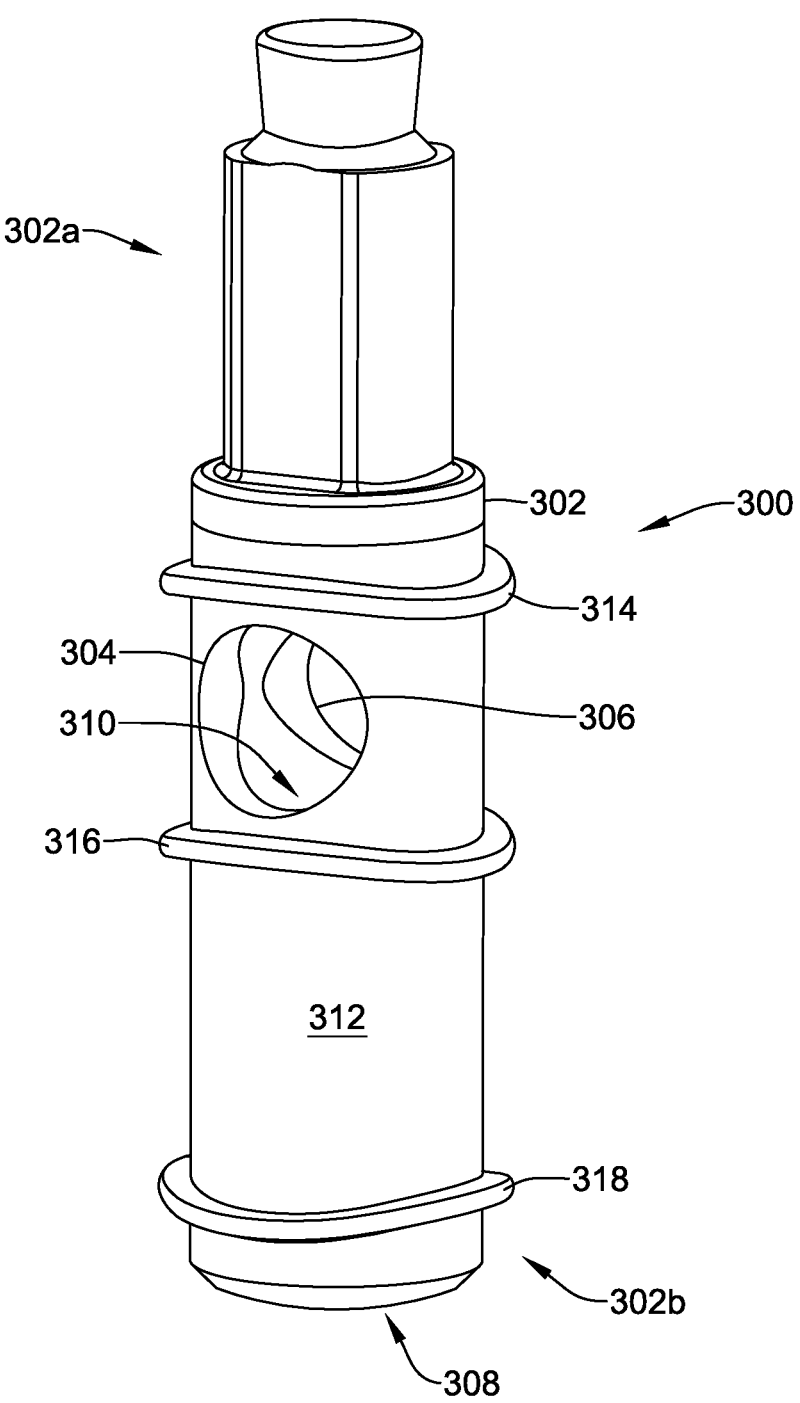
FIG. 6 depicts a schematic perspective view of an illustrative valve stem.
Figure 7:
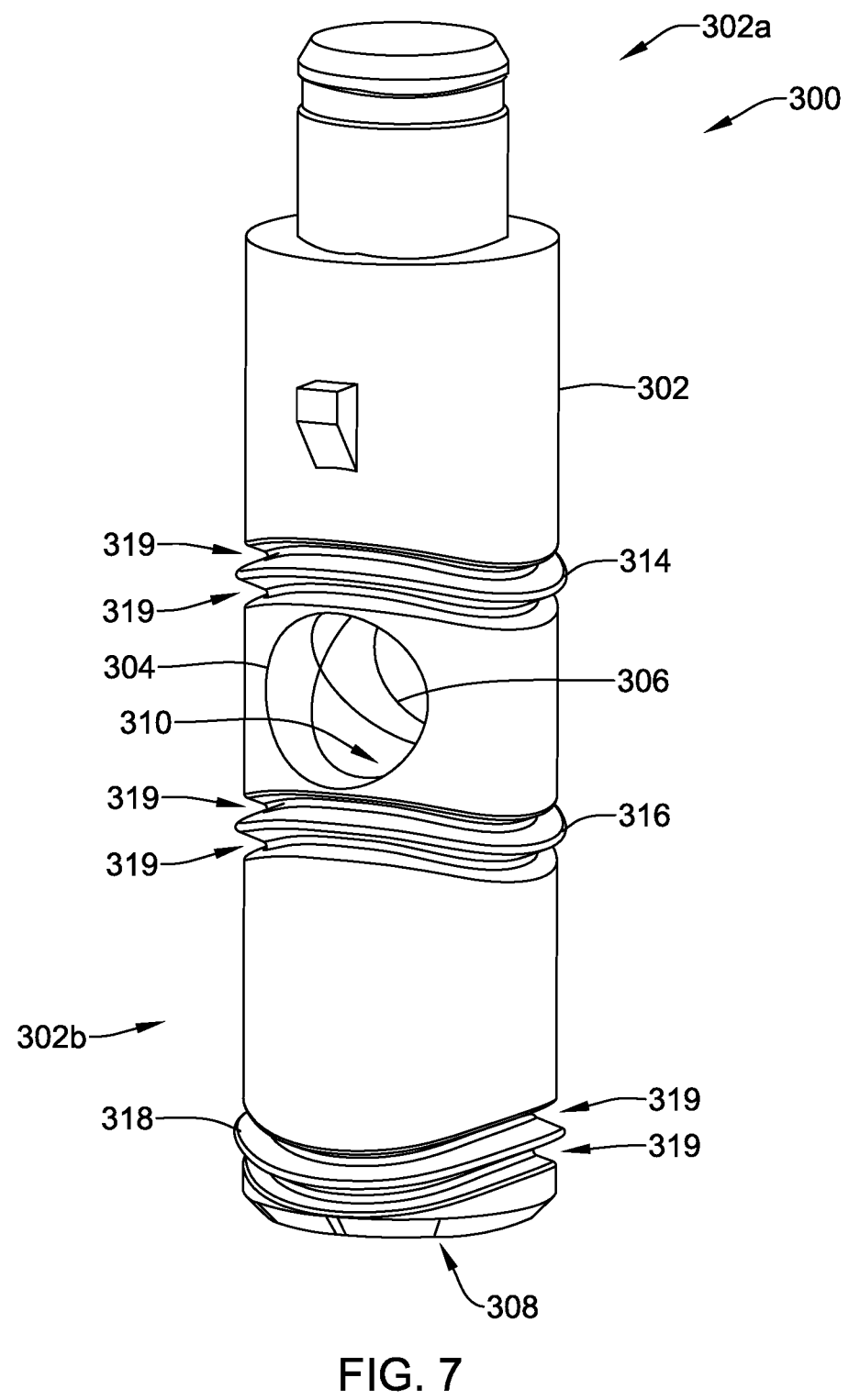
FIG. 7 depicts a schematic perspective view of an illustrative valve stem.

FIGS. 6 and 7 depict perspective views of illustrative valve stems 300 in which the seals 314, 316, 318 are monolithic with (e.g. monolithically formed with) the elongate body 302, where the seals 314, 316, 318 have sealing surfaces 321 that are circumferentially non-perpendicular with the longitudinal axis A of the elongate body 302. The illustrative valve stem 300 depicted in FIG. 6 omits recesses 319 at or proximate the seals 314, 316, 318. The illustrative valve stem 300 depicted in FIG. 7 includes proximal and distal recesses 319 proximate the seals 314, 316, 318. Valve stems 300 in which the seals 314, 316, 318 are monolithic with the elongate body 302 are described, for example, in U.S. patent application Ser. No. 18/485,771, filed on Oct. 12, 2023, titled VALVE AND VALVE COMPONENTS FOR AN ENDOSCOPE, which is hereby incorporated by reference in its entirety for any and all purposes.

FIGS. 8-12 depict schematic partial views of illustrative configurations of the valve stem 300 within illustrative configurations of the valve well 320, where a seal 313 having a sealing surface 321 extends circumferentially around the elongate body 302 and is non-perpendicular to the longitudinal axis A of the elongate body 302. In FIGS. 8-12, the elongate body 302 and the seal 313 of the valve stem 300 are depicted from a side view and the valve well 320 is depicted in cross-section.

The valve well 320 is depicted as including the inner wall 323 and one or more openings (e.g., one or more first openings 330 (e.g., inflow or outflow openings) and one or more second openings 332 (e.g., the other of inflow or outflow openings)), where the one or more openings may be similar to or different than the proximal opening 322, the distal opening 324, and intermediate opening 326 discussed above. The first openings 330, the second openings 332, and/or other suitable features of the valve well 320 and/or the elongate body 302 may be opposed from one another and/or may be located at other suitable spaced-apart locations from one another. In one example, at least some of the first openings 330, the second openings 332, and/or other features of the valve well 320 may be disposed at about ninety-degrees from one another and/or at one or more other suitable angles from one another.

The seal 313 may be configured similarly to the seals 314, 316, 318 and/or have features similar to the features of the seals 314, 316, 318 described above. Although not shown in FIGS. 8-12, the depicted configurations of the elongate body 302 may include one or more recesses 319, as described above. The seals 313 depicted in FIGS. 8-12 are configured based on locations of openings in the valve well 320 and to have sealing surfaces 321 that are non-perpendicular to the longitudinal axis A. The seals 313 may be symmetric about a plane separating a front and a back view of the valve stem 300, such that the seal 313 has the same configuration on the depicted side of the valve stem 300 as on the not-depicted side of the valve stem 300, but this is not required.

Figures 8, 9:
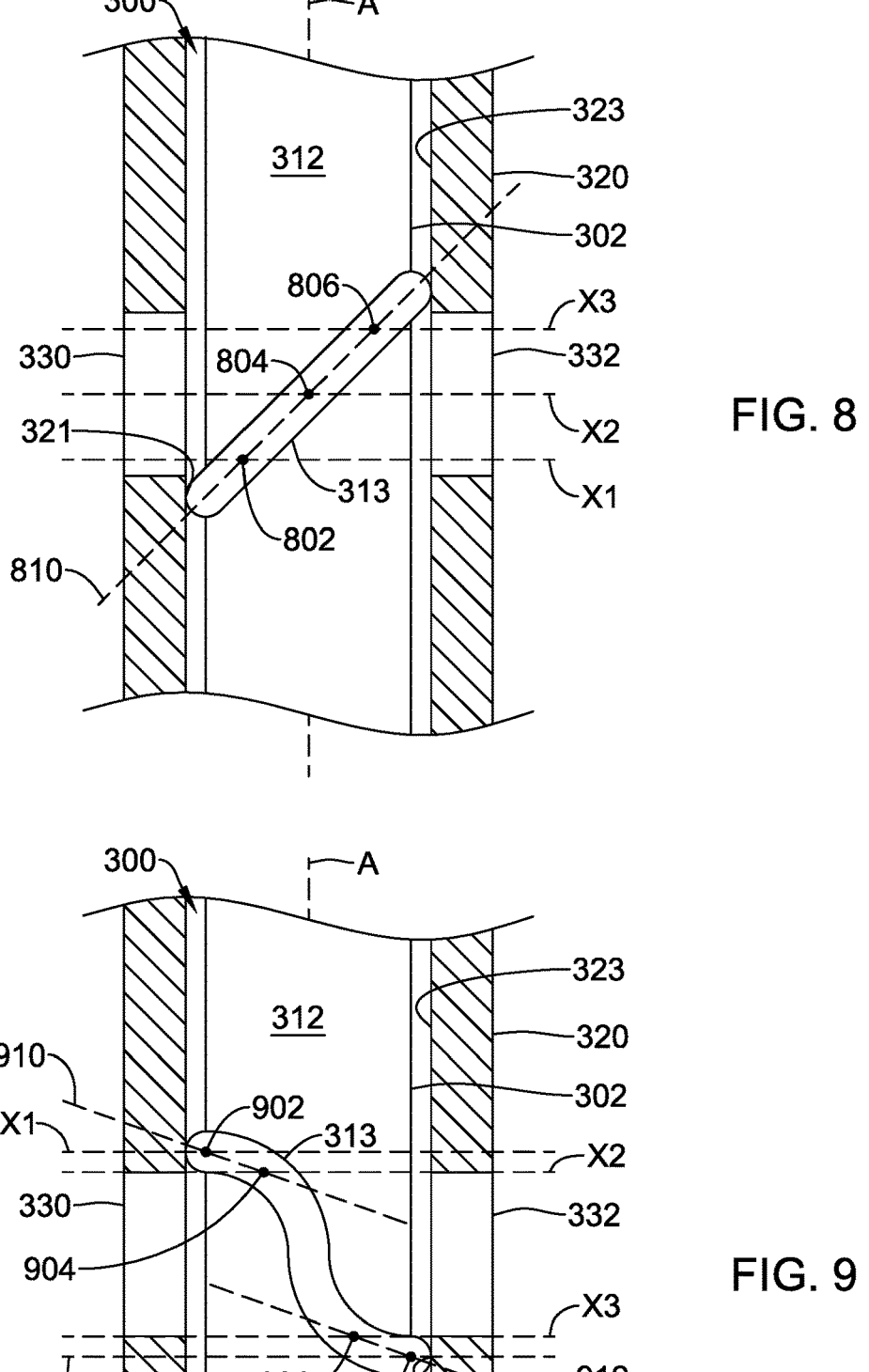
FIGS. 8-12 depict schematic views of illustrative seal configurations on a valve stem within a valve well.

The configuration of the valve stem 300 in the valve well 320 depicted in FIG. 8 depicts an illustrative configuration of the seal 313 having a circumferentially planar sealing surface 321 that is non-perpendicular to the longitudinal axis A of the elongate body 302 and fluidly sealing the first opening 330 from the second opening 332. The sealing surface 321 depicted in FIG. 8 engages the surface of the inner wall 323 at a location distal of the first opening 330 and at a location proximal of the second opening 332 to fluidly seal the first opening 330 from the circumferentially opposed second opening 332 of the valve well 320, where the first opening 330 and the second opening 332 are at a same axial location along the longitudinal axis A.

FIG. 8 depicts three points 802, 804, 806 on an outer-most circumference of the sealing surface 321 of the seal 313. As depicted in FIG. 8, a first point 802 is at a first axial position $X_1$, a second point 804 is at a second axial position $X_2$ proximal of the first axial position $X_1$, and a third point 806 is at a third axial position $X_3$ proximal of the second axial position $X_2$. Because two or more of the points 802, 804, 806 are at different axial positions, the sealing surface 321 and/or the seal 313 may be considered to be non-perpendicular with the longitudinal axis A.

The three points 802, 804, 806 depicted in FIG. 8 are in a single plane 810, along with the other points along the outer-most circumference of the sealing surface 321 of the seal 313, when connected with a point in space (e.g., into or out of the paper at an axial location of one of the points on the outer-most circumference of the sealing surface 321). As a result, the sealing surface 321 and/or the seal 313 may be planar.

The configuration of the valve stem 300 in the valve well 320 depicted in FIG. 9 includes an illustrative configuration of the seal 313 having a circumferentially non-planar sealing surface 321 that is non-perpendicular to the longitudinal axis A of the elongate body 302 and fluidly sealing the first opening 330 from the second opening 332. The sealing surface 321 depicted in FIG. 9 engages the surface of the inner wall 323 at a location proximal of the first opening 330 and at a location distal of the second opening 332 to fluidly seal the first opening 330 from the circumferentially opposed second opening 332 of the valve well 320, where the first opening 330 and the second opening 332 are at a same axial location along the longitudinal axis A.

FIG. 9 depicts four points 902, 904, 906, 908 on an outer-most circumference of the sealing surface 321 of the seal 313. As depicted in FIG. 9, a first point 902 is at a first axial position $X_1$, a second point 904 is at a second axial position $X_2$ distal of the first axial position $X_1$, a third point 906 is at a third axial position $X_3$ distal of the second axial position $X_2$, and a fourth point 908 is at a fourth axial position $X_4$ distal of the third axial point $X_3$. Because two or more of the points 902, 904, 906, 908 are at different axial positions, the sealing surface 321 and/or the seal 313 depicted in FIG. 9 may be considered to be non-perpendicular with the longitudinal axis A.

The four points 902, 904, 906, 908 depicted in FIG. 9, are in two separate planes 910, 912. For example, the first point 902 and the second point 904, along with at least a third point (e.g., where the third point may be in space and is not necessarily on the seal 313) at the same axial position as one of the first point 902 and the second point 904 define a first plane 910, and the third point 906 and the fourth point 908, along with at least a third point (e.g., where the third point may be in space and is not necessarily on the seal 313) at the same axial position as one of the third point 906 and the fourth point 908 define a second plane 912 that is not the same plane as the first plane 910. As a result, the sealing surface 321 and/or the seal 313 may be non-planar because the points on the outer-most circumference of the sealing surface 321 define two or more planes when connected with a point in space (e.g., into or out of the paper at an axial location of one of the points on the outer-most circumference of the sealing surface 321).

Figures 10, 11:
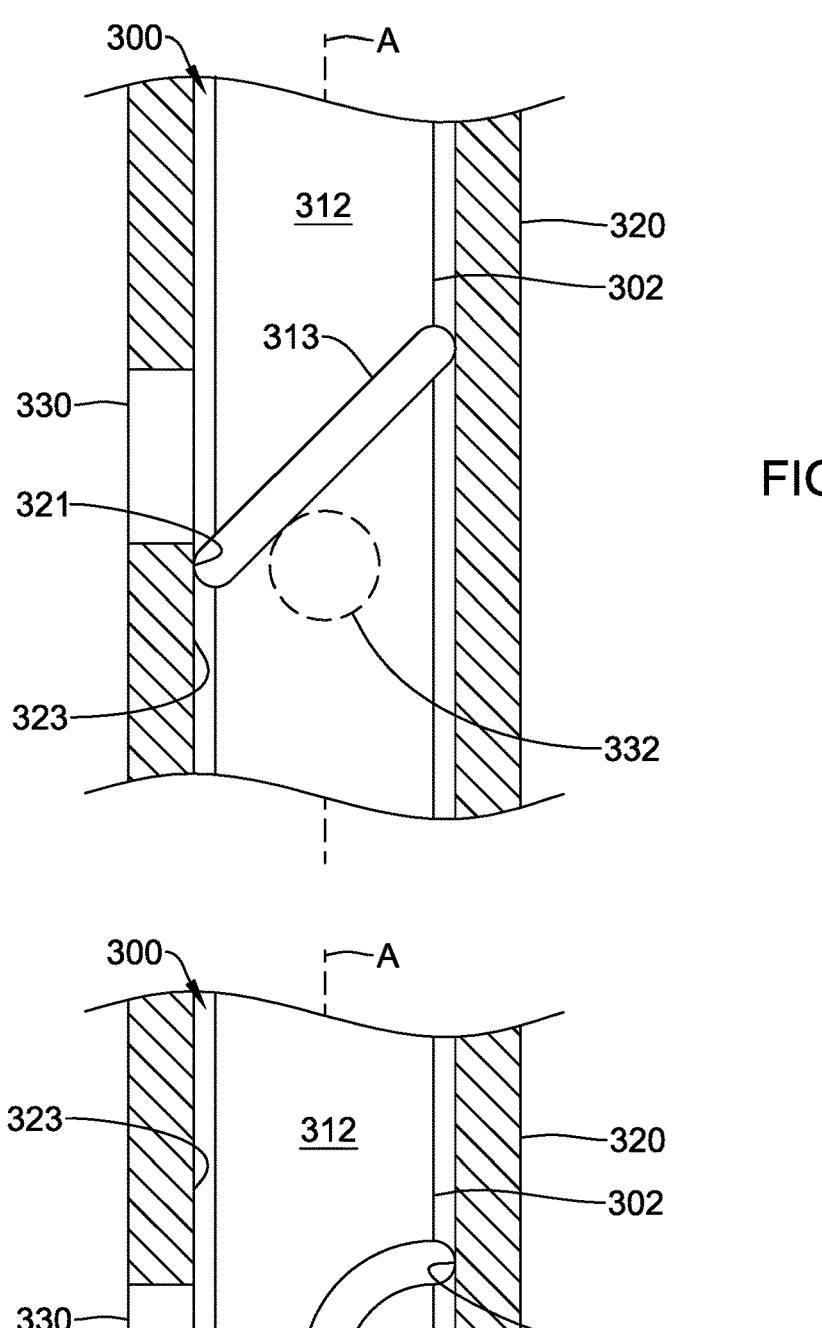

The configuration of the valve stem 300 in the valve well 320 depicted in FIG. 10 includes an illustrative configuration of the seal 313 having a circumferentially planar sealing surface 321 that is non-perpendicular to the longitudinal axis A of the elongate body 302 and fluidly sealing the first opening 330 from the axially spaced second opening 332 (depicted in broken lines in FIG. 10 because the second opening 332 is behind the elongate body 302). The sealing surface 321 depicted in FIG. 10 engages the surface of the inner wall 323 at a location distal of the first opening 330 and at a location proximal of the second opening 332 (not fully depicted in FIG. 10 because the second opening 332 is on a back side of the valve well 320) to fluidly seal the first opening 330 from the second opening 332 circumferentially offset by ninety degrees or about ninety degrees from the first opening 330, where the second opening 332 is at an axial location distal of a location of the first opening 330. In some cases and although not required, an axial location of an opening 330, 332 may be determined from an axial location of a center of the opening 330, 332.

The configuration of the valve stem 300 in the valve well 320 depicted in FIG. 11 includes an illustrative configuration of the seal 313 having a circumferentially non-planar sealing surface 321 that is non-perpendicular to the longitudinal axis A of the elongate body 302 and fluidly sealing the first opening 330 from the axially spaced second opening 332 (depicted in broken lines in FIG. 11 because the second opening 332 is behind the elongate body 302). The sealing surface 321 depicted in FIG. 11 engages the surface of the inner wall 323 at a location distal of the first opening 330 and at a location proximal of the second opening 332 (not fully depicted in FIG. 11 because the second opening 332 is on a back side of the valve well 320) to fluidly seal the first opening 330 from the second opening 332 circumferentially offset by ninety degrees or about ninety degrees from the first opening 330, where the second opening 332 is at an axial location distal of a location of the first opening 330.

Figure 12:
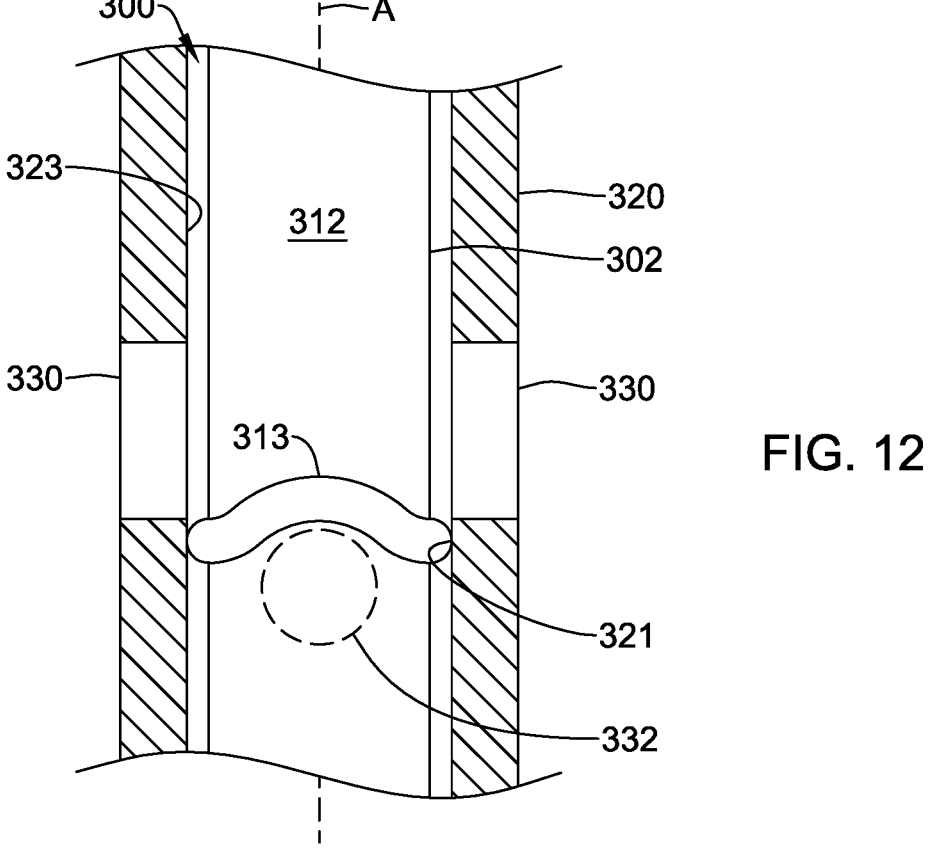

The configuration of the valve stem 300 in the valve well 320 depicted in FIG. 12 includes an illustrative configuration of the seal 313 having a circumferentially non-planar sealing surface 321 that is non-perpendicular to the longitudinal axis A of the elongate body 302 and fluidly sealing two circumferentially opposed first openings 330 from an axially spaced second opening 332 (depicted in broken lines in FIG. 12 because the second opening 332 is behind the elongate body 302). The sealing surface 321 depicted in FIG. 12 engages the surface of the inner wall 323 at a location distal of the first openings 330 and at a location proximal of the second opening 332 (not fully depicted in FIG. 12 because the second opening 332 is on a back side of the valve well 320) to fluidly seal the first openings 330 from the second opening 332 circumferentially offset by ninety degrees or about ninety degrees from each of the first opening 330, where the second opening 332 is at an axial location distal of an axial location of the first openings 330.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A valve stem for a medical device, the valve stem comprises:
   an elongate body;
   a first opening in the elongate body;
   a second opening in the elongate body;

a lumen extending from the first opening to the second opening; and
a seal extending circumferentially around the elongate body and defining a sealing surface, and
wherein the sealing surface is non-perpendicular with a longitudinal axis of the elongate body and defines a wave extending circumferentially around the elongate body.

2. The valve stem of claim 1, further comprising:
   a groove defining a surface of the elongate body and extending circumferentially around the elongate body, and
   wherein the groove is non-perpendicular with the longitudinal axis of the elongate body and the seal is within the groove.

3. The valve stem of claim 1, wherein the wave comprise two peaks and two valleys.

4. The valve stem of claim 1, wherein the seal is a first seal and the sealing surface is a first sealing surface, the valve stem further comprises:
   a second seal extending circumferentially around the elongate body and defining a second sealing surface; and
   wherein the second sealing surface is non-perpendicular with the longitudinal axis of the elongate body.

5. The valve stem of claim 4, wherein the first sealing surface is parallel to the second sealing surface.

6. The valve stem of claim 4, wherein the first sealing surface is non-parallel to the second sealing surface.

7. The valve stem of claim 4, further comprising:
   a third seal extending circumferentially around the elongate body and defining a third sealing surface; and
   wherein the third sealing surface is non-perpendicular with the longitudinal axis of the elongate body.

8. The valve stem of claim 1, wherein the elongate body and the seal are monolithic.

9. The valve stem of claim 1, wherein the elongate body is formed from a thermoplastic elastomer (TPE).

10. A valve stem for a medical device, the valve stem is configured to translate within a valve well of the medical device, the valve stem comprises:
    an elongate body;
    a first opening in the elongate body;
    a second opening in the elongate body;
    a lumen extending from the first opening to the second opening;
    a first seal extending circumferentially around the elongate body and defining a first sealing surface, the first seal is proximal of the first opening; and
    a second seal extending circumferentially around the elongate body and defining a second sealing surface, the first seal is distal of the first opening, and
    wherein the first sealing surface and the second sealing surface are non-perpendicular with a longitudinal axis of the elongate body and one or both of the first sealing surface and the second sealing surface define a wave extending circumferentially around the elongate body.

11. The valve stem of claim 10, wherein one or both of the first sealing surface and the second sealing surface are planar.

12. The valve stem of claim 10, wherein one or both of the first sealing surface and the second sealing surface are non-planar.

13. The valve stem of claim 10, further comprising:
    a third seal extending circumferentially around the elongate body and defining a third sealing surface, and wherein one or more of the first sealing surface, the second sealing surface, and the third sealing surface are parallel to a least one other of the first sealing surface, the second sealing surface, and the third sealing surface.

14. A medical device comprising:

a proximal handle;

a distal tip unit adapted to be inserted into a body cavity of a patient;

an elongate tube extending between the proximal handle and the distal tip unit; and a valve in communication with a lumen of the elongate tube to adjust a fluid flow to the distal tip unit via the lumen, the valve comprises:

a valve well having an interior wall, a first opening, and a second opening; and a valve stem configured to adjust within the valve well, the valve stem comprising an elongate body and a seal defining a sealing surface defining a wave extending circumferentially around the elongate body, and wherein the sealing surface is configured to engage the interior wall at a first location proximal of the first opening and at a second location distal of the second opening, the second location is circumferentially spaced from the first location.

15. The medical device of claim 14, wherein:

the elongate body includes a groove defining an outer surface of the elongate body and extending circumferentially around the elongate body; and the seal extends circumferentially around the elongate body within the groove.

16. The medical of device claim 14, wherein:

the seal is a first seal and the sealing surface is a first sealing surface, the valve stem further comprises a second seal extending circumferentially around the elongate body and defining a second sealing surface; and the second sealing surface is configured to engage the interior wall at a location distal of the first opening and the second opening.

17. The medical device of claim 14, wherein the elongate body includes a groove defining an outer surface of the elongate body and a wave extending circumferentially around the elongate body.

18. The medical device of claim 1, wherein the elongate body includes a groove defining an outer surface of the elongate body and a wave extending circumferentially around the elongate body.

19. The medical device of claim 10, wherein the elongate body includes a groove defining an outer surface of the elongate body and a wave extending circumferentially around the elongate body.

* * * * *